United States Patent [19]

Kugler et al.

[11] 4,206,134

[45] Jun. 3, 1980

[54] RUTHENIUM SUPPORTED ON MANGANESE OXIDE AS HYDROCARBON SYNTHESIS CATALYSTS IN CO/$H_2$ REACTIONS

[75] Inventors: Edwin L. Kugler, Summit; Samuel J. Tauster, Englishtown; Shun C. Fung, Edison, all of N.J.

[73] Assignee: Exxon Research & Engineering Co., Florham Park, N.J.

[21] Appl. No.: 19,352

[22] Filed: Mar. 12, 1979

[51] Int. Cl.$^2$ .................................................. C07C 1/04
[52] U.S. Cl. ........................... 260/449 R; 260/449 M; 252/444; 252/456; 252/454; 252/463; 252/461; 252/471
[58] Field of Search ....................... 260/449 R, 449 M

[56] References Cited

U.S. PATENT DOCUMENTS 3,941,820   3/1976   Jackson et al. .................... 260/449.6

FOREIGN PATENT DOCUMENTS 762412   4/1976   South Africa ........................ 260/449.6
762413   4/1976   South Africa ........................ 260/449.6

OTHER PUBLICATIONS

Bussemier et al., "Lower Olefins via Fisher-Tropsch", Hydrocarbon Processing, vol. 55, pp. 105–112 (1976).

*Primary Examiner*—Howard T. Mars
*Attorney, Agent, or Firm*—Joseph J. Allocca

[57] ABSTRACT

An improved method is disclosed for the selective synthesis of low molecular weight olefins, particularly $C_2$ and $C_3$ olefins inclusive, which method comprises the steps of passing a CO and $H_2$ synthesis gas stream over a catalyst at a temperature and pressure and for a time sufficient to generate the desired olefinic products, wherein the improvement consists in using as a catalyst ruthenium on a support selected from the group consisting of a manganese oxide, other manganese-containing oxides or mixtures of various manganese oxides. The weight loading of the ruthenium may range from about 0.01 to about 15 wt. % based on the total catalyst weight. The operating conditions of the instant process are the standard Fischer-Tropsch synthesis reaction parameters, preferably an $H_2$/CO mole ratio of from about 10 to about 0.1, a space velocity of from about 100 hr$^{-1}$ to about 50,000 hr$^{-1}$, a temperature of from about 100° C. to about 500° C. and a pressure of from about 103 to about $1.03 \times 10^5$ kPa (103 kPa - 1 atm). The instant process is also marked by a reduced methane make.

10 Claims, No Drawings

RUTHENIUM SUPPORTED ON MANGANESE OXIDE AS HYDROCARBON SYNTHESIS CATALYSTS IN CO/H₂ REACTIONS

BRIEF DESCRIPTION OF THE INVENTION

The instant invention is an improved method for the selective synthesis of low molecular weight olefins, particularly $C_2$ and $C_3$ olefins inclusive, which method comprises the steps of passing a CO and $H_2$ synthesis gas stream over a catalyst at a temperature and pressure and for a time sufficient to generate the desired olefinic products, wherein the improvement consists in using as a catalyst ruthenium on a support selected from the group consisting of a manganese oxide, other manganese-containing oxides or mixtures of various manganese oxides. The weight loading of the ruthenium may range from about 0.01 to about 15 wt. % based on the total catalyst weight. The operating conditions of the instant process are the standard Fischer-Tropsch synthesis reaction parameters, preferably an $H_2$/CO mole ratio of from about 10 to about 0.1, a space velocity of from about 100 hr. to about 50,000 $hr^{-1}$, a temperature of from about 100° to about 500° C. and a pressure of from about 103 to about $1.03 \times 10^5$ kPa (103 kPa=1 atm). The instant process is also marked by a reduced methane make.

DESCRIPTION OF THE INVENTION

This invention relates to a new method for the selective synthesis of low molecular weight olefins especially $C_2$ and $C_3$ olefins from CO and $H_2$ which comprises passing a typical synthesis gas over a catalyst at standard Fischer-Tropsch reaction conditions, the improvement comprising using as the catalyst ruthenium on a support selected from the group consisting of a manganese oxide, other manganese containing oxide and mixtures thereof, preferably MnO. In particular, the process comprises passing a synthesis gas stream consisting of CO and $H_2$ wherein the $H_2$/CO mole ratio ranges from about 10 to 0.1, preferably about 3 to 0.25, most preferably about 2 to 0.5 at a space velocity of from about 100 $hr^{-1}$ to about 2 to 0.5 at a space velocity of from about 100 $hr^{-1}$ to about 50,000 $hr^{-1}$, preferably about 3,000 $hr^{-1}$ to about 10,000 $hr^{-1}$ over a catalyst comprising from about 0.01 to about 15 wt. % preferably about 0.1 to about 5 wt. %, most preferably about 0.5 to about 3 wt. % ruthenium on a support selected from the group consisting of a manganese oxide, other manganese containing oxides and mixtures thereof, preferably MnO, at a temperature of from about 100° to 500° C., preferably about 150°-450° C., most preferably about 250°-350° C., and at a pressure of from about 103 to about $1.03 \times 10^5$ kPa, preferably about 103 to about 3090 kPa, most preferably about 103 to about 2060 kPa (103 kPa=1 atm) for a time sufficient to generate the desired olefinic products. The instant process is superior to prior art methods employing ruthenium on alumina in that the instant process exhibits a marked reduction in methane make while yielding greatly improved volumes of $C_2$ to $C_4$ hydrocarbon products which $C_2$-$C_4$ hydrocarbon products contain a very high concentration of $C_2$-$C_3$ olefins. This selectivity to olefins can be enhanced by running at the lower $H_2$/CO ratios, preferably between 3 to 0.25, most preferably 2 to 0.5.

In the practice of the instant invention, the catalyst is described as being ruthenium supported on a material selected from the group consisting of a manganese oxide, other manganese containing oxides and mixtures thereof. In particular, this means that the support is selected from the group consisting of MnO, $Al_2O_3$-MnO, $SiO_2$-MnO, MnO-Carbon, Group IVB-manganese oxides, Group VB-manganese oxides, Group IA (alkali metal)-manganese oxides, Group IIA (alkaline earth metal)-manganese oxides and rare earth-manganese oxides and mixtures thereof. The preferred support is MnO. With most supported metal catalysts, the higher the surface area of the support, the higher the dispersion of the supported metal at a given metal loading. It is therefore desirable to use an MnO or other recited support with as high a surface area as possible to maximize the dispersion of the ruthenium metal. The supports will therefore typically possess surface areas ranging from between 1 to 200 $m^2g^{-1}$, preferably from 50 to 200 $m^2g^{-1}$.

The supported ruthenium catalysts employed in the practice of the instant process are themselves prepared by techniques known in the art for the preparation of other catalyst systems such as ruthenium on $Al_2O_3$, $SiO_2$, carbon, etc. A suitable ruthenium salt, such as ruthenium nitrate, ruthenium acetate, ruthenium chloride, chlororuthenic acid, etc., is dissolved in a suitable solvent system (such as water, or any suitable solvent) and stirred with the chosen manganese oxide support system. After thorough mixing, the mixture is either allowed to dry and then heated in air at a temperature of from 100° to 150° C. or alternatively may be dried in a single step by heating in air at between 100° to 150° C. for several hours.

A final step which must be practiced involves heat treating the supported ruthenium catalysts prepared as outlined above, or by any number of similar preparative techniques, in a reducing atmosphere such as hydrogen or a hydrogen containing atmosphere, at a temperature greater than about 300° C., preferably about 400° C., most preferably greater than about 500° C. for from typically 0.5 to 4 hours, preferably 1-2 hours. Serial No. 019,494 filed even date herewith describes this technique in detail and is hereby incorporated by reference. It should be noted that this heat treating reduction step need not be practiced as a separate step since the Fischer-Tropsch reaction is practiced in a reducing atmosphere (a hydrogen containing atmosphere) and will therefore, have a similar reducing effect on the catalyst as the above step. Should the $H_2$/CO ratio be too low to effect the reduction, i.e., should the $H_2$ concentration be too low, a separate reducing step will be needed.

EXAMPLES

Synthesis of 1% Ru/MnO

MnO was impregnated, using the method of incipient wetness, with an aqueous solution of $RuCl_3$ of such concentration as to provide 1% (wt) of ruthenium (calculated as the metal) in the finished catalyst. The impregnate was dried at about 110° C., then reduced in situ in flowing $H_2$ at 450° C. for 1 hr.

Catalytic Use of Ru/MnO Systems

Comparisons were run using Ru/MnO and Ru/$Al_2O_3$ (and MnO alone) as Fischer-Tropsch catalysts at various $H_2$/CO ratios, temperatures and pressures. The results are presented in Tables I to VI. In each situation, it can be seen that under equivalent conditions of metal loading, temperature pressure and $H_2$/CO ratios, the Ru/MnO catalyst yielded less methane and operates volumes of $C_2$-$C_4$ in general, of which a substantial proportion was olefinic.

TABLE I

Product Distributions of Supported Ruthenium Catalysts for $H_2$ + CO Reaction

| | Hydrocarbon Products (Wt. %) | | | | |
|---|---|---|---|---|---|
| | $C_1$ | $C_2$ | $C_3$ | $C_4$ | $C_5$ |
| 1% Ru/MnO | 37 | 30 | 20 | 10 | 4 |
| 5% Ru/$Al_2O_3$ | 76 | 14 | 5 | 3 | 1 |

T = 300–305° C.; P = 1.1 atm; $H_2$/CO = 3.

TABLE II

Olefin-Paraffin Distribution in Products

| | Ethylene/Ethane Ratio | | |
|---|---|---|---|
| $H_2$/CO = | 3 | 2.4 | 1.6 |
| 1% Ru/MnO | 0.8 | 1.1 | 2.1 |
| 5% Ru/$Al_2O_3$ | 0.08 | — | — |

| | Propylene/Propane Ratio | | |
|---|---|---|---|
| $H_2$/CO = | 3 | 2.4 | 1.6 |
| 1% Ru/MnO | 7 | 25 | 100 |
| 5% Ru/$Al_2O_3$ | — | — | — |

T = 300–305° C; P = 1.1 atm; $H_2$/CO = 1.6–3.0

TABLE III

Selectivity of Ruthenium Catalysts
(Reaction Conditions: $H_2$/CO = 3, Pressure = 103 kPa)

| Catalyst | Temp. (°C.) | % Conv. | Product Carbon Number | Total Wt. % | Wt. % Olefin | Wt. % Paraffin |
|---|---|---|---|---|---|---|
| 1% Ru/MnO | 350 | 4.7 | $C_1$ | 48 | — | — |
| | | | $C_2$ | 32 | 17 | 15 |
| | | | $C_3$ | 18 | 16 | 2 |
| | | | $C_4^+$ | 2 | — | — |
| 1% Ru/$Al_2O_3$ | 353 | 5.5 | $C_1$ | 76 | — | — |
| | | | $C_2$ | 18 | 4 | 14 |
| | | | $C_3$ | 5 | 5 | trace |
| | | | $C_4^+$ | 1 | — | — |

TABLE IV

Selectivity of Ruthenium Catalysts
(Reaction Conditions: $H_2$/CO = 1, Pressure = 103 kPa)

| Catalyst | Temp. (°C.) | % Conv. | Product Carbon Number | Total Wt. % | Wt. % Olefin | Wt. % Paraffin |
|---|---|---|---|---|---|---|
| 1% Ru/MnO | 348 | 3.4 | $C_1$ | 27 | — | — |
| | | | $C_2$ | 34 | 28 | 6 |
| | | | $C_3$ | 35 | 35 | trace |
| | | | $C_4^+$ | 4 | — | — |
| 1% Ru/$Al_2O_3$ | 350 | 5.3 | $C_1$ | 58 | — | — |
| | | | $C_2$ | 26 | 11 | 15 |
| | | | $C_3$ | 13 | 13 | trace |
| | | | $C_4^+$ | 3 | — | — |

TABLE V

Selectivity of Ruthenium Catalysts
(Reaction Conditions: $H_2$/CO = 0.5, Pressure = 103 kPa)

| Catalyst | Temp. (°C.) | % Conv. | Product Carbon Number | Total Wt. % | Wt. % Olefin | Wt. % Paraffin |
|---|---|---|---|---|---|---|
| 1% Ru/MnO | 351 | 4.7 | $C_1$ | 20 | — | — |
| | | | $C_2$ | 37 | 30 | 7 |
| | | | $C_3$ | 33 | 33 | trace |
| | | | $C_4^+$ | 9 | — | — |
| 1% Ru/$Al_2O_3$ | 351 | 6.8 | $C_1$ | 48 | — | — |
| | | | $C_2$ | 32 | 13 | 19 |
| | | | $C_3$ | 18 | 18 | trace |
| | | | $C_4^+$ | 2 | — | — |

TABLE VI

Selectivity of Ruthenium Catalysts
(Reaction Conditions $H_2$/CO = 3, Pressure = 103 kPa)

| Catalyst | Temp. (°C.) | % Conv. | $CH_4$ | $C_2H_4$ | $C_2H_6$ | $C_3H_6$ | $C_3H_8$ | $C_4^+$ |
|---|---|---|---|---|---|---|---|---|
| 1% Ru/MnO | 350 | 4.7 | 48 | 17 | 15 | 16 | 2 | 2 |
| 1% Ru/$Al_2O_3$ | 353 | 5.5 | 76 | 4 | 14 | 5 | trace | 1 |
| MnO | 352 | 0.0 | — | — | — | — | — | — |
| 1% Fe/MnO | 349 | 0.0 | — | — | — | — | — | — |

What is claimed is:

1. A process for the enhanced synthesis of $C_2$-$C_4$ olefins with reduced production of methane comprising the steps of passing $H_2$ and CO in an $H_2$/CO ratio of from about 10 to about 0.1 over a catalyst reduced at a temperature greater than about 300° C. comprising ruthenium on a manganese-containing oxide support, wherein said manganese-containing oxide support is selected from the group consisting of MnO, $Al_2O_3$-MnO, $SiO_2$-MnO, MnO-carbon, Group IVB-manganese oxide, Group VB-manganese oxides, Group IA-manganese oxides, Group IIA-manganese oxides, rare earth-manganese oxides and mixtures thereof, at a space velocity of from about 100 $hr^{-1}$ to about 50,000 $hr^{-1}$, at a temperature of from about 100° C. to about 500° C., at a pressure of from about 103 to about $1.03 \times 10^5$ kPa for a time sufficient to effect the generation of the desired olefinic product, wherein the concentration of said ruthenium in said catalyst is from about 0.01 to about 15% by weight.

2. The process of claim 1 wherein the manganese containing oxide is MnO.

3. The process of claim 1 or 2 wherein the $H_2$/CO ratio is from about 3 to about 0.25, the temperature is from about 150° C. to about 450° C., the pressure is from about 103 to about 3090 kPa and the space velocity is about 3000 $hr^{-1}$ to about 10,000 $hr^{-1}$.

4. The process of claim 1 or 2 wherein the $H_2$/CO ratio is from about 2 to about 0.5, the temperature is from about 250° C. to about 350° C., the pressure is from about 103 to about 2060 kPa.

5. The process of claim 1 or 2 wherein the ruthenium loading is from about 0.1 to about 5 wt. %.

6. The process of claim 3 wherein the ruthenium loading is from about 0.1 to about 5 wt. %.

7. The process of claim 4 wherein the ruthenium loading is from about 0.1 to about 5 wt. %.

8. The process of claim 1 or 2 wherein the ruthenium loading is from about 0.5 to about 3 wt. %.

9. The process of claim 3 wherein the ruthenium loading is from about 0.5 to about 3 wt. %.

10. The process of claim 4 wherein the ruthenium loading is from about 0.5 to about 3 wt. %.